United States Patent
Ogasawara

(10) Patent No.: US 8,835,885 B2
(45) Date of Patent: Sep. 16, 2014

(54) CHARGED PARTICLE BEAM IRRADIATION DEVICE

(71) Applicant: Sumitomo Heavy Industries, Ltd., Tokyo (JP)

(72) Inventor: Tsuyoshi Ogasawara, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/134,657

(22) Filed: Dec. 19, 2013

(65) Prior Publication Data

US 2014/0158915 A1    Jun. 12, 2014

Related U.S. Application Data

(63) Continuation of application No. PCT/JP2012/065386, filed on Jun. 15, 2012.

(30) Foreign Application Priority Data

Jun. 28, 2011    (JP) .................................. 2011-142691

(51) Int. Cl.
*A61N 5/00* (2006.01)
*G21K 5/04* (2006.01)
*A61N 5/10* (2006.01)
*G21K 5/02* (2006.01)

(52) U.S. Cl.
CPC .. *G21K 5/02* (2013.01); *G21K 5/04* (2013.01); *A61N 5/1042* (2013.01); *A61N 2005/1087* (2013.01); *A61N 2005/1095* (2013.01); *A61N 5/1077* (2013.01)
USPC ..................................... 250/492.3; 250/492.1

(58) Field of Classification Search
None
See application file for complete search history.

(56) References Cited

U.S. PATENT DOCUMENTS

6,863,733 B1 *   3/2005   Tanabe .......................... 118/722
2009/0065351 A1 *   3/2009   Nuss ........................ 204/192.15

FOREIGN PATENT DOCUMENTS

| JP | S63-124395 A | | 5/1988 | |
| JP | 05055032 A | * | 3/1993 | ............... H01F 7/22 |
| JP | H05-055032 A | | 3/1993 | |
| JP | 2004-361096 A | | 12/2004 | |
| JP | 2004361096 A | * | 12/2004 | ............... G21K 5/00 |
| JP | 2007-229025 A | | 9/2007 | |
| JP | 2007229025 A | * | 9/2007 | |

* cited by examiner

*Primary Examiner* — Andrew Smyth
(74) *Attorney, Agent, or Firm* — Rader, Fishman & Grauer PLLC

(57) ABSTRACT

A charged particle beam irradiation device includes an accelerator that accelerates charged particles and emits a charged particle beam; an irradiation unit that irradiates a body with the charged particle beam; a duct that transports the charged particle beam to the irradiation unit; a tubular body arranged on a propagation path of the charged particle beam within the irradiation unit, has inert gas filled thereinto, and has particle beam transmission films transmitting the charged particle beam therethrough at an inlet and an outlet thereof; a gas supply unit that supplies the inert gas into the tubular body; and a leak valve that leaks the inert gas inside the tubular body to the outside when the internal pressure of the tubular body is equal to or higher than a set pressure. The gas supply unit has a plurality of supply lines having different amounts of supply of inert gas.

2 Claims, 2 Drawing Sheets

US 8,835,885 B2

CHARGED PARTICLE BEAM IRRADIATION DEVICE

INCORPORATION BY REFERENCE

Priority is claimed to Japanese Patent Application No. 2011-142691, filed Jun. 28, 2011, and International Patent Application No. PCT/JP2012/065386, the entire content of each of which is incorporated herein by reference.

BACKGROUND

1. Technical Field

The present invention relates to a charged particle beam irradiation device that irradiates a body to be irradiated with a charged particle beam.

2. Description of the Related Art

In the related art, a charged particle beam irradiation device disclosed in the related art is known as the charged particle beam irradiation device used for radiation therapy. The related art describes a particle beam treatment device that scans a charged particle beam by a scanning method and irradiates a body to be irradiated, such as a part of body with cancer, with the beam and that includes an inert gas chamber that is provided on a path of the charged particle beam, an integral gas supply pipe that supplies inert gas into the inert gas chamber, and a control device that controls the amount of gas supply of a gas supply pipe based on the difference between the internal and external pressures of the inert gas chamber.

In the aforementioned particle beam treatment device, isolating films are provided at an inlet and an outlet of the inert gas chamber to secure airtightness, and inert gas is supplied into the inert gas chamber to prevent damage of the isolating films by the difference between the internal and external pressures. Also, by arranging this inert gas chamber on the path of the charged particle beam, scattering of the charged particle beam under the influence of air is avoided and thus, irradiation position accuracy is improved.

SUMMARY

According to an embodiment of the present invention, there is provided a charged particle beam irradiation device including an accelerator configured to accelerate charged particles and emit a charged particle beam; an irradiation unit configured to irradiate a body to be irradiated with the charged particle beam; a duct configured to transport the charged particle beam emitted from the accelerator to the irradiation unit; a tubular body that is arranged on a propagation path of the charged particle beam within the irradiation unit, has inert gas filled therein, and has particle beam transmission films transmitting the charged particle beam therethrough at an inlet and an outlet thereof; a gas supply unit configured to supply the inert gas into the tubular body; and a leak valve configured to leak the inert gas inside the tubular body to the outside when the internal pressure of the tubular body is equal to or higher than a set pressure. The gas supply unit has a plurality of supply lines having different amounts of supply of inert gas.

DETAILED DESCRIPTION

Figure 1:
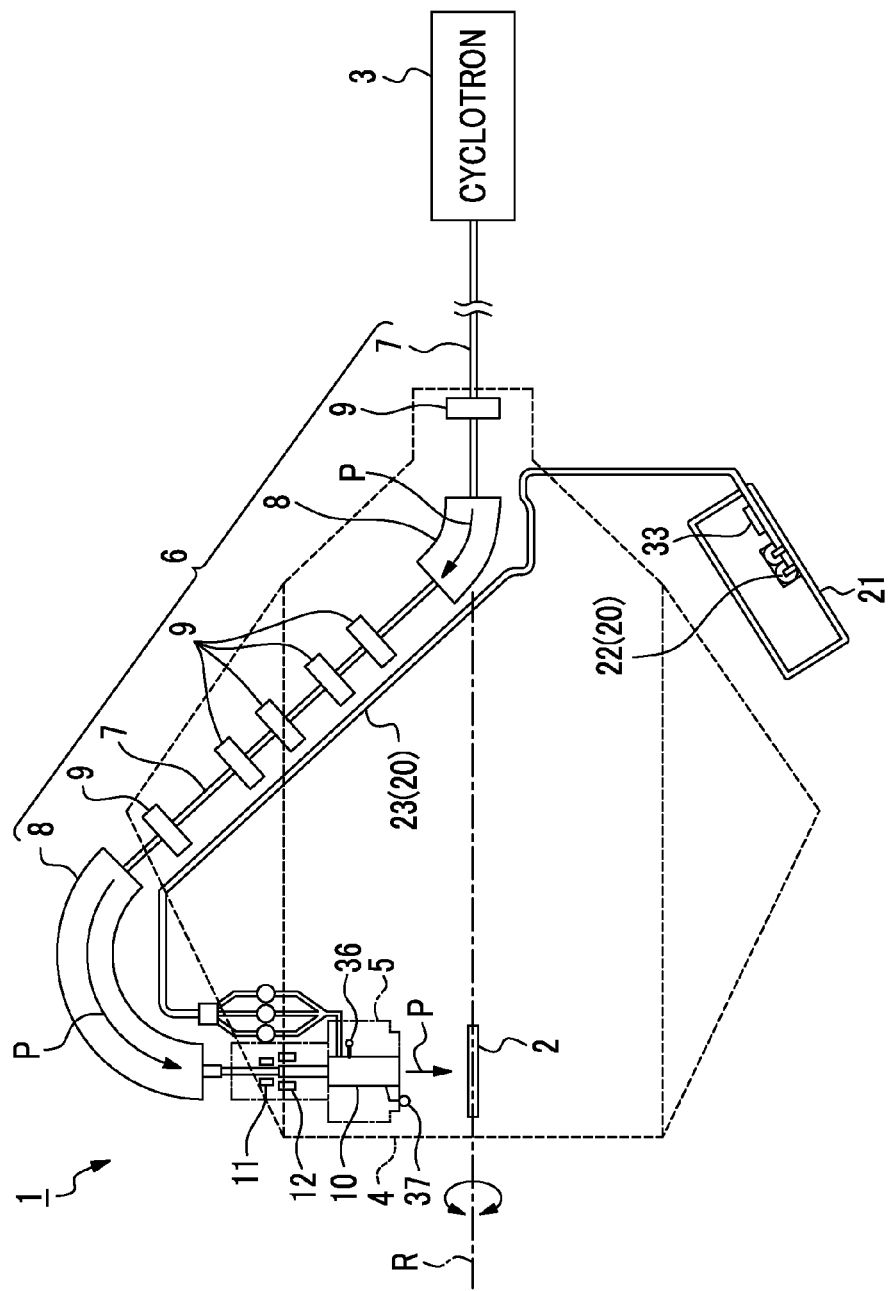
FIG. 1 is a schematic view showing a charged particle beam irradiation device related to an embodiment of the invention.

In the particle beam irradiation device of the related art mentioned above, to realize the control of the amount of supply of the inert gas, there are problems because it is necessary to provide a control device that determines a gas flow rate based on the difference between the internal and external pressures of the inert gas chamber, an actuator for driving the flow control valve of the gas supply pipe, or the like and in that the configuration or control of the device is complicated.

Thus, it is desirable to provide a charged particle beam irradiation device that can manage the amount of gas supply to a tubular body with a simple configuration.

According to the charged particle beam irradiation device related to the embodiment of the invention, since there is almost no necessity for changing the amount of supply of the inert gas to the tubular body in normal use, the amount of gas supply to the tubular body can be easily managed by adopting a configuration in which a line with a suitable amount of supply is selected from the plurality of supply lines based on a situation. Moreover, according to the charged particle beam irradiation device, compared to the configuration of the related art in which the amount of supply is always controlled, the amount of supply of the inert gas to the tubular body can be managed with an extremely simple configuration. Additionally, since the inert gas is leaked through the leak valve when the internal pressure of the tubular body rises excessively, it is easy to manage the internal pressure of the tubular body within a desired range.

In the charged particle beam irradiation device related to the embedment of the invention, the plurality of supply lines may include a pressure-maintaining supply line for maintaining the pressure inside the tubular body at a predetermined value, an adjusting supply line for adjusting the pressure within the tubular body, and a substituting supply line for substituting air inside the tubular body with the inert gas, the amount of supply of the inert gas of the adjusting supply line is larger than the amount of supply of the inert gas of the pressure-maintaining supply line, and the amount of supply of the inert gas of the substituting supply line may be larger than the amount of supply of the inert gas of the adjusting supply line.

According to the charged particle beam irradiation device related to the embodiment of the invention, management of the amount of gas supply based on a situation can be realized by performing gas supply by the pressure-maintaining supply line at a normal time and using the adjusting supply line with a slightly larger amount of supply at the time of adjustment, such as maintenance. Additionally, when the air inside the tubular body is substituted with the inert gas, at the time of setting of the device, efficient substitution of the inert gas is possible by using the substituting supply line with a large amount of supply.

The charged particle beam irradiation device related to the embodiment of the invention may further include a suction pump configured to suction air inside the tubular body, and the suction pump suctions the air inside the tubular body, using at least one supply line among the plurality of supply lines.

According to the charged particle beam irradiation device related to the embodiment of the invention, the air inside the tubular body can be suctioned using the supply lines of the gas supply unit when the air inside the tubular body is substituted with the inert gas. Thus, it is not necessary to separately provide a line for the pump, and reduction in the number of pipes and simplification of the configuration of the device can be achieved.

A preferred embodiment of the invention will be described below in detail with reference to the drawings. In addition, the terms "upstream" and "downstream" mean the upstream (cyclotron side) and downstream (patient side) of a charged particle beam to be emitted, respectively.

As shown in FIG. 1, the charged particle beam irradiation device 1, which is a device used for cancer treatment through radiotherapy, or the like, includes a treatment table 2 on which a patient is put. In the charged particle beam irradiation device 1, irradiation of a charged particle beam P emitted from a cyclotron (accelerator) 3 is performed to a tumor (a body to be irradiated) of a patient on the treatment table 2. The charged particle beam P is obtained by accelerating particles with charges at high speed, for example, is a proton, a heavy particle (heavy ion) beam, or the like.

The charged particle beam irradiation device 1 includes a rotating gantry 4 that is rotatable 360 degrees around the treatment table 2 with a rotation axis R as a center, an irradiation nozzle (irradiation unit) 5 that is attached to the interior of the rotating gantry 4 and is movable to arbitrary rotational positions by the rotating gantry 4, and a beam transportation line 6 that connects the cyclotron 3 and the irradiation nozzle 5 together.

The beam transportation line 6 is a path along which the charged particle beam P emitted from the cyclotron 3 is transported to the irradiation nozzle 5. The beam transportation line 6 includes a vacuum duct 7 through which the charged particle beam P passes. The interior of the vacuum duct 7 is maintained in vacuum, and the charged particle beam P under transportation is prevented from being scattering due to air or the like.

Additionally, the beam transportation line 6 includes a deflecting magnet 8 that deflects the charged particle beam P along the vacuum duct 7, and a converging magnet 9 that converges the beam diameter of the charged particle beam P under transportation.

The irradiation nozzle 5 irradiates a diseased part of the patient on the treatment table 2 with the charged particle beam P. The irradiation nozzle 5 is detachably configured with respect to the rotating gantry 4. The irradiation nozzle 5 has an extension duct (tubular body) 10 connected to the vacuum duct 7 of the beam transportation line 6, and a quadrapole magnet 11 and a scanning magnet 12 arranged around the extension duct 10.

The quadrapole magnet 11 is provided to converge the beam diameter of the charged particle beam P, which has entered the extension duct 10, with a magnetic field. The scanning magnet 12 is provided to scan the charged particle beam P that has entered the extension duct 10 and handles the charged particle beam as a scanning beam.

Figure 2:
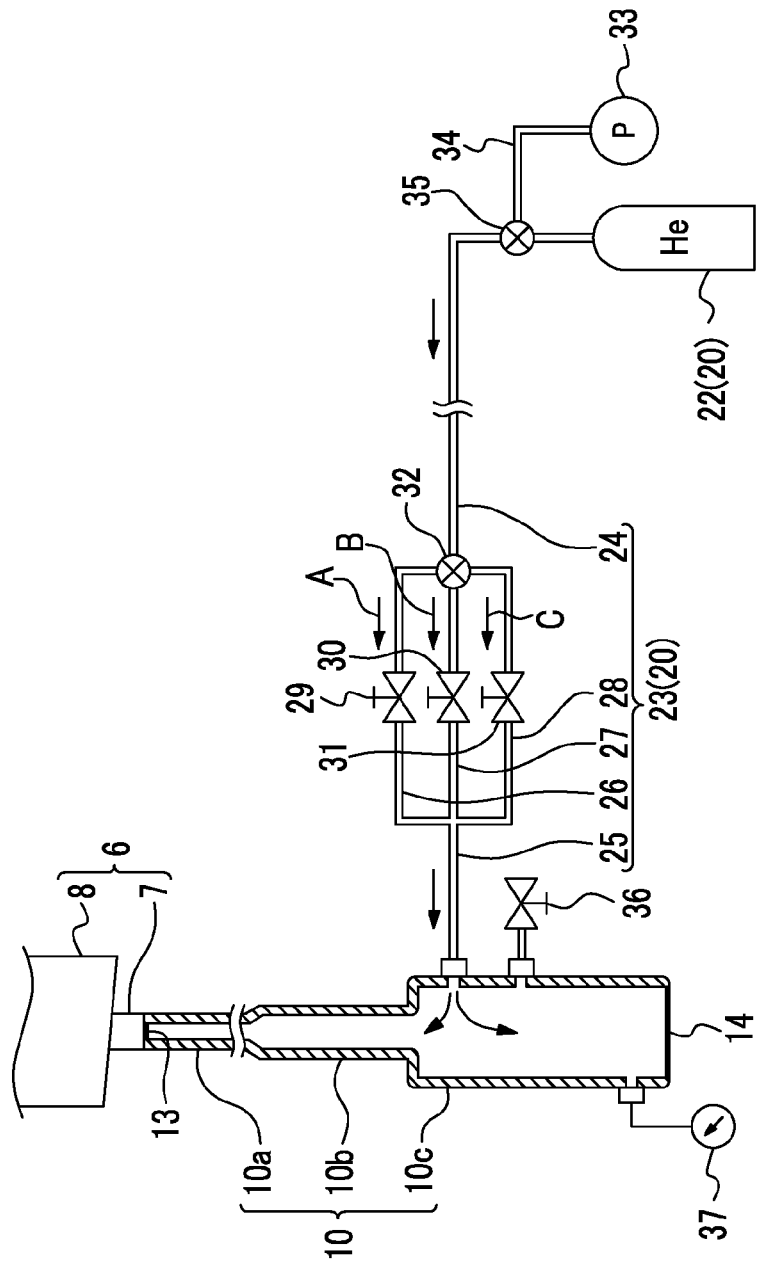
FIG. 2 is a view for describing an extension duct and a gas supply line of FIG. 1.

As shown in FIGS. 1 and 2, the extension duct 10 is a hollow member arranged on a propagation path of the charged particle beam P within the irradiation nozzle 5. Helium gas (inert gas) is filled into the extension duct 10.

The extension duct 10 is constituted by an inlet portion 10a through which the charged particle beam P enters from the vacuum duct 7, a central portion 10b that is scanned with the charged particle beam P by the scanning magnet 12, and an outlet portion 10c through which the charged particle beam P is irradiated toward the patient.

The inlet portion 10a, the central portion 10b, and the outlet portion 10c are cylindrical portions, respectively, and the diameters (thicknesses) thereof become larger in order of the inlet portion 10a, the central portion 10b, and the outlet portion 10c. Since it is necessary to secure a scanning space for the scanning beam more widely as the extension duct 10 is closer to the patient, internal spaces are more widely formed in order of the inlet portion 10a, the central portion 10b, and the outlet portion 10c.

Kapton films (particle beam transmission films) (kapton is a registered trademark) 13 and 14 for trapping the helium gas within the extension duct 10 are arranged at the inlet of the inlet portion 10a, and the outlet of the outlet portion 10c. The kapton films 13 and 14 have properties of isolating the helium gas within the extension duct 10 from the external atmosphere and transmitting the charged particle beam P therethrough.

Although the kapton films 13 and 14 can transmit the charged particle beam P therethrough without attenuating the charged particle beam due to their thinness, since the strength thereof decreases based on thinness, there is a possibility that the films may be damaged if the difference between the internal and external pressures of the extension duct 10 becomes large. The possibility of the damage occurring is particularly large in the kapton film 14 on the outlet side with a large cross-sectional diameter. Additionally, since a small amount of helium gas leaks through the kapton films 13 and 14 from the extension duct 10, it is necessary to supply the helium gas into the extension duct 10.

The charged particle beam irradiation device 1 has a gas supply unit 20 that supplies the helium gas into the extension duct 10. The gas supply unit 20 is constituted by a helium gas container 22 that is installed at a deck 21 outside the rotating gantry 4, and a supply pipe 23 that connects the helium gas container 22 and the extension duct 10 together.

The deck 21 is provided independently from the rotating gantry 4, and the position of the helium gas container 22 is constant irrespective of the rotation of the rotating gantry 4. In addition, the helium gas container 22 may be fixed to the rotating gantry.

The supply pipe 23 is constituted by a gas-container-side pipe 24, a duct-side pipe 25, and first to third pipes 26 to 28. The gas-container-side pipe 24 is connected to the helium gas container 22, and helium gas is introduced from the helium gas container 22. The duct-side pipe 25 is connected to the outlet portion 10c of the extension duct 10, and the introduced helium gas is supplied to the extension duct 10.

The first pipe 26, the second pipe 27, and the third pipe 28 are pipes that are provided in parallel between the gas-container-side pipe 24 and the duct-side pipe 25. One ends of the first to third pipes 26 to 28 branch in three ways with a three-way valve 32 provided at the end of the gas-container-side pipe 24 as a starting point, and the other ends of the first to third pipes 26 to 28 are collectively connected to the duct-side pipe 25. Pipes into which the helium gas flows is switched by operating the three-way valve 32. Additionally, the first to third pipes 26 to 28 include valves 29, 30, and 31 which determine the amounts of gas supply, respectively.

The gas supply unit 20 has a pressure-maintaining supply line A, an adjusting supply line B, and a substituting supply line C. Here, the supply lines mean not pipes themselves but flow channels through which the helium gas flows.

The pressure-maintaining supply line A is a supply line for maintaining the pressure within the extension duct 10 at a predetermined value at a normal time. As this predetermined value, for example, a pressure slightly higher than the atmospheric pressure is selected. The pressure-maintaining supply line A is constituted by the gas-container-side pipe 24, the duct-side pipe 25, and the first pipe 26.

In the pressure-maintaining supply line A, the helium gas of the helium gas container 22 moves in order of the gas-container-side pipe 24, the first pipe 26, and the duct-side pipe 25, and is supplied into the extension duct 10. In addition, the gas-container-side pipe 24 and the duct-side pipe 25 are pipes that are common in the respective supply lines.

The amount of supply of the helium gas by the pressure-maintaining supply line A is set to such an amount (for example, 0.5 L/min) that the pressure within the extension duct 10 can be maintained at a pressure slightly higher than the atmospheric pressure. This amount of supply is fixed to a constant value by the valve 29 of the first pipe 26.

The adjusting supply line B is a supply line used at the time of when the pressure adjustment of the extension duct 10, such as maintenance. The adjusting supply line B is constituted by the gas-container-side pipe 24, the duct-side pipe 25, and the second pipe 27.

In the adjusting supply line B, the helium gas to the helium gas container 22 moves in order of the gas-container-side pipe 24, the second pipe 27, and the duct-side pipe 25 and is supplied into the extension duct 10. The amount of supply of the helium gas in the adjusting supply line B is set to a larger value (for example, 2.0 L/min) than the amount of gas supply of the pressure-maintaining supply line A. This amount of supply is fixed to a constant value by the valve 30 of the second pipe 27.

The substituting supply line C is a supply line used when air within the extension duct 10 is substituted with the helium gas. The substituting supply line C is constituted by the gas-container-side pipe 24, the duct-side pipe 25, and the third pipe 28.

In the substituting supply line C, the helium gas to the helium gas container 22 moves in order of the gas-container-side pipe 24, the third pipe 28, and the duct-side pipe 25 and is supplied into the extension duct 10. The amount of supply of the helium gas in the substituting supply line C is set to a larger value (for example, 10 L/min) than the adjusting supply line B. This amount of supply is fixed to a constant value by the valve 31 of the third pipe 28. The amount of supply of the helium gas in the substituting supply line C is preferably equal to or higher than 10 times of the amount of supply of the pressure-maintaining supply line A.

In the pressure-maintaining supply line A, the adjusting supply line B, and the substituting supply line C, only one line selected by switching of the three-way valve 32 is used. In addition, the arrangement or configuration of the pressure-maintaining supply line A, the adjusting supply line B, and the substituting supply line C are not limited to that shown in FIG. 2.

The charged particle beam irradiation device 1 includes a suction pump 33 for suctioning the air within the extension duct 10. The suction pump 33 is used when the air within the extension duct 10 is substituted with the helium gas.

A suction pipe 34 is connected to a suction port of the suction pump 33, and the suction pipe 34 is connected to a switching valve 35 provided in the middle of the gas-container-side pipe 24. By switching the switching valve 35, a flow channel connected to the helium gas container 22 is closed and a flow channel connected to the suction pump 33 is opened. By driving the suction pump 33 in this state, suction of the air within the extension duct 10 is performed. The suction pump 33 performs suction of the air within the extension duct 10, using any of the pressure-maintaining supply line A, the adjusting supply line B, and the substituting supply line C.

Additionally, the charged particle beam irradiation device 1 includes a leak valve 36 that leaks the helium gas to the exterior of the extension duct 10 when the internal pressure is equal to or higher than a set pressure. The leak valve 36 is provided at the outlet portion 10c of the extension duct 10.

The set pressure of the leak valve 36 is preferably set within a range of 1.5 times to 2 times the atmospheric pressure. By providing such a leak valve 36, it is possible to prevent a situation where the helium gas is superfluously supplied into the extension duct 10 due to the difference between the internal and external pressures of the extension duct 10 becomes large and the kapton films 13 and 14 are torn off.

Additionally, the charged particle beam irradiation device 1 includes a pressure gauge 37 that displays the internal pressure of the extension duct 10. The pressure gauge 37 is attached to a side surface of the outlet portion 10c of the extension duct 10. A meter display unit of the pressure gauge 37 protrudes from the irradiation nozzle 5 and is arranged at a position that is easily seen from a treatment room within the rotating gantry 4.

The meter display unit of the pressure gauge 37 shows a value higher than the atmospheric pressure through the supply of gas from the pressure-maintaining supply line A at a normal time. If abnormality, such as gas leak, occurs in the extension duct 10, the meter display unit of the pressure gauge 37 drops to the atmospheric pressure, and thereby, the abnormality of the extension duct 10 is detected. In addition, various internal pressure sensors may be adopted instead of the pressure gauge.

According to the charged particle beam irradiation device 1 related to the present embodiment described above, since it is not essentially necessary to change the amount of supply of the helium gas to the extension duct 10 in normal use, the amount of gas supply to the extension duct 10 can be easily managed by adopting a configuration in which a line with a suitable amount of supply is selected from the three supply lines A to C based on a situation. Additionally, since the helium gas is leaked through the leak valve when the internal pressure of the extension duct 10 rises excessively, it is easy to manage the internal pressure of the extension duct 10 within a desired range.

Moreover, according to the charged particle beam irradiation device 1, compared to the configuration of the related art in which the amount of supply is always controlled, it is not necessary to provide an actuator or the like that drives a complicated control device or valve, and the amount of supply of the helium gas to the extension duct 10 can be managed with an extremely simple configuration. Additionally, since a complicated control device is not used, a control system trouble can be avoided, highly reliable management of the amount of gas supply can be realized, and the manufacturing costs of the device can be reduced from simplification.

Additionally, in the charged particle beam irradiation device 1, management of the amount of gas supply based on a situation can be realized by performing gas supply by the pressure-maintaining supply line A at a normal time and using the adjusting supply line B with a slightly larger amount of supply at the time of adjustment, such as maintenance. Additionally, when the air within the extension duct 10 is substituted with the helium gas, such as at the time of setting of the device, efficient substitution of the helium gas is allowed by using the substituting supply line C with a large amount of supply.

Moreover, according to the charged particle beam irradiation device 1, air suction can be performed using the supply lines A to C for the helium gas when the air within the extension duct 10 is suctioned by the suction pump 33. Thus, it is not necessary to separately provide a line for the pump, and reduction in the number of pipes and simplification of the configuration of the device can be achieved.

The invention is not limited to the aforementioned embodiment.

For example, not the rotating gantry 4 that rotates 360 degrees but a gantry that can only oscillate less than 360 degrees (for example, 180 degrees) may be used for the charged particle beam irradiation device 1. Additionally, instead of the rotation irradiation using the rotating gantry, stationary irradiation in which the rotating gantry is not used and the irradiation nozzle is fixed may be used. The invention can also be effectively applied to the stationary irradiation.

Additionally, the accelerator may be a synchrotron, a synchrocyclotron, a linear accelerator, or the like.

Additionally, although the management of the amount of gas supply in the charged particle beam irradiation device 1 can mainly be manually performed, an aspect in which the management is controlled automatically, such as switching a supply line based on the difference between the internal and external pressures of the extension duct 10, can be adopted.

Additionally, films that partition off the interior and exterior of the extension duct 10 are not limited to the kapton films 13 and 14. Moreover, the films or sheets that are thin to a degree where the strength of the charged particle beam P to pass is not affected may be used, and can secure the airtightness within the extension duct 10. Moreover, the gas filled into the extension duct 10 is not limited to the helium gas, and rare gas and other suitable inert gas may be used.

The invention is available for the charged particle beam irradiation device that can manage the amount of gas supply to a tubular body with a simple configuration.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation device comprising:
an accelerator configured to accelerate charged particles and emit a charged particle beam;
an irradiation unit configured to irradiate a body to be irradiated with the charged particle beam;
a duct configured to transport the charged particle beam emitted from the accelerator to the irradiation unit;
a tubular body that is arranged on a propagation path of the charged particle beam within the irradiation unit, has inert gas filled thereinto, and has particle beam transmission films transmitting the charged particle beam therethrough at an inlet and an outlet thereof;
a gas supply unit configured to supply the inert gas into the tubular body; and
a leak valve configured to leak the inert gas inside the tubular body to the outside when the internal pressure of the tubular body is equal to or higher than a set pressure; and
a leak line that connects the tubular body and the leak valve;
wherein the gas supply unit comprises:
an inert gas container configured to supply the inert gas;
a plurality of supply lines having different amounts of supply of inert gas; and
an inert gas container side line that connects the inert gas container and each of the supply lines;
wherein the plurality of supply lines include a pressure-maintaining supply line configured to maintain the pressure inside the tubular body at a predetermined value, an adjusting supply line configured to adjust the pressure within the tubular body, and a substituting supply line configured to substitute an air inside the tubular body with the inert gas, and
wherein the amount of supply of the inert gas of the adjusting supply line is larger than the amount of supply of the inert as of the pressure-maintaining supply line, and the amount of supply of the inert gas of the substituting supply line is larger than the amount of supply of the inert gas of the adjusting supply line.

2. The charged particle beam irradiation device according to claim 1, further comprising:
a suction pump configured to suction air inside the tubular body,
wherein the suction pump suctions the air inside the tubular body, using at least one supply line among the plurality of supply lines.

* * * * *